United States Patent
Nihongi et al.

(10) Patent No.: US 9,605,574 B2
(45) Date of Patent: Mar. 28, 2017

(54) UREA WATER PIPE CLOGGING DETECTION DEVICE FOR UREA SELECTIVE CATALYTIC REDUCTION

(71) Applicant: ISUZU MOTORS LIMITED, Tokyo (JP)

(72) Inventors: Shigeru Nihongi, Yokohama (JP); Masanobu Minezawa, Yokohama (JP)

(73) Assignee: ISUZU MOTORS LIMITED, Tokyo (JP)

( * ) Notice: Subject to any disclaimer, the term of this patent is extended or adjusted under 35 U.S.C. 154(b) by 121 days.

(21) Appl. No.: 14/763,676

(22) PCT Filed: Jan. 15, 2014

(86) PCT No.: PCT/JP2014/050564
§ 371 (c)(1),
(2) Date: Oct. 6, 2015

(87) PCT Pub. No.: WO2014/115620
PCT Pub. Date: Jul. 31, 2014

(65) Prior Publication Data
US 2016/0040577 A1    Feb. 11, 2016

(30) Foreign Application Priority Data
Jan. 28, 2013    (JP) .................................. 2013-013388

(51) Int. Cl.
*F01N 3/20*    (2006.01)
*F01N 11/00*    (2006.01)
(Continued)

(52) U.S. Cl.
CPC ............ *F01N 3/2066* (2013.01); *F01N 11/00* (2013.01); *G01K 13/02* (2013.01);
(Continued)

(58) Field of Classification Search
CPC ............................... F01N 3/2066; F01N 3/208
(Continued)

(56) References Cited

U.S. PATENT DOCUMENTS

2010/0242439 A1*    9/2010    Domon .............. B01D 53/9431
                                                          60/274
2013/0055700 A1    3/2013    Minezawa et al.
(Continued)

FOREIGN PATENT DOCUMENTS

JP    2011-247137    12/2011
JP    2012-2061    1/2012

OTHER PUBLICATIONS

Extended European Search Report dated Nov. 9, 2016 in corresponding European Patent Application No. 14743090.4.
(Continued)

*Primary Examiner* — Walter L Lindsay, Jr.
*Assistant Examiner* — Philip Marcus T Fadul
(74) *Attorney, Agent, or Firm* — Staas & Halsey LLP

(57) ABSTRACT

A clogging detection device includes a urea water sensor which detects temperature in a urea water tank, a pressure sensor which detects pressure in a urea water feed line, an exhaust gas temperature sensor disposed in an exhaust pipe upstream of a selective catalytic reduction device, and a determination unit. When a key switch is turned on, the determination unit performs a startup control to drive a supply pump and increase the pressure in a pipe segment extending to a dosing value. If a detection value of the exhaust gas temperature sensor is no greater than a predetermined temperature, and a detection value of the urea water sensor is no smaller than a freezing temperature, then the determination unit performs emptying control for returning the urea water from the pipe segment to the urea water
(Continued)

tank to detect clogging of the pipe segment from the detection value of the pressure sensor.

13 Claims, 3 Drawing Sheets

(51) Int. Cl.
*G01K 13/02* (2006.01)
*G01N 33/00* (2006.01)
*G01N 33/18* (2006.01)

(52) U.S. Cl.
CPC ......... *G01N 33/0037* (2013.01); *G01N 33/18* (2013.01); *F01N 2550/05* (2013.01); *F01N 2610/02* (2013.01); *F01N 2610/1473* (2013.01); *F01N 2610/1486* (2013.01); *F01N 2610/1493* (2013.01); *F01N 2900/0421* (2013.01); *F01N 2900/1404* (2013.01); *F01N 2900/1808* (2013.01); *F01N 2900/1811* (2013.01); *G01K 2013/024* (2013.01); *G01K 2013/026* (2013.01); *Y02T 10/24* (2013.01); *Y02T 10/47* (2013.01)

(58) Field of Classification Search
USPC .......................................................... 73/49.5
See application file for complete search history.

(56) References Cited

U.S. PATENT DOCUMENTS

2013/0064716 A1  3/2013  Fukuoka et al.
2013/0269321 A1* 10/2013  Watanabe ............... F01N 3/208
                                                                60/274

OTHER PUBLICATIONS

PCT International Preliminary Report on Patentability issued Jul. 28, 2015 in corresponding International Patent Application No. PCT/JP2014/050564.
PCT Written Opinion of the International Searching Authority mailed Apr. 15, 2014 in corresponding International Patent Application No. PCT/JP2014/050564.
Patent Abstracts of Japan, Publication No. 2011-247137, published Dec. 8, 2011.
Patent Abstracts of Japan, Publication No. 2012-2061, published Jan. 5, 2012.
International Search Report mailed on Apr. 15, 2014 in corresponding International Patent Application No. PCT/JP2014/050564.

* cited by examiner

UREA WATER PIPE CLOGGING DETECTION DEVICE FOR UREA SELECTIVE CATALYTIC REDUCTION

CROSS-REFERENCE TO RELATED APPLICATIONS

This application is a U.S. National Stage Application, which claims the benefit under 35 U.S.C. §371 of PCT International Patent Application No. PCT/JP2014/050564, filed Jan. 15, 2014, which claims the foreign priority benefit under 35 U.S.C. §119 of Japanese Patent Application No. 2013-013388, filed Jan. 28, 2013, the contents of which are incorporated herein by reference.

TECHNICAL FIELD

The present invention relates to a urea selective catalytic reduction ("SCR") system for selectively reducing NOx contained in an exhaust gas of an engine with urea water, and more particularly to a urea water pipe clogging detection device for urea SCR that can detect whether clogging of urea water occurs in piping extending to a dosing valve adapted to spray urea water.

BACKGROUND ART

An SCR system that uses a selective reduction catalyst is developed as an exhaust gas purification system to purify NOx contained in an exhaust gas of a diesel engine This SCR system supplies urea water, which is retained or pooled in a urea water tank, to an upstream exhaust gas of an SCR device to hydrolyze the urea water with the heat of the exhaust gas and generate ammonia. The SCR system then uses the ammonia to reduce NOx with a catalyst inside the SCR device, thereby purifying the exhaust gas. The urea water is sprayed from a dosing valve disposed upstream of the SCR device to supply the urea water to the upstream exhaust gas of the SCR device.

Feeding of the urea water to the dosing valve is carried out by a supply module that includes a supply module pump (SM pump), a urea water pressure sensor and other components. The supply module is connected to the urea water tank via a draw-in line (suction line), and supplies the urea water, which is drawn in from the urea water tank via the draw-in line, to the dosing valve through a pressurized urea water feed line extending between the supply module and the dosing valve. The dosing valve is controlled by a DCU (dosing control unit) such that opening and closing of the dosing valve is controlled in response to a detection value of a NOx sensor disposed downstream of the SCR device to adjust an amount of urea to be sprayed (urea spray volume).

LISTING OF REFERENCES

PATENT LITERATURE 1: Japanese Patent Application Laid-Open Publication No. 2011-247137
PATENT LITERATURE 2: Japanese Patent Application Laid-Open Publication No. 2012-2061

SUMMARY OF THE INVENTION

Problems to be Solved by the Invention

When the dosing valve for spraying (injecting) the urea water into the NOx catalyst is clogged with a foreign matter and/or the pressurized urea water feed line extending to the dosing valve is clogged with a foreign matter, the urea water spraying does not take place. Thus, it is possible for the NOx sensor disposed downstream of the SCR device to detect (determine) whether or not the clogging has occurred by detecting whether or not the SCR purification rate is abnormal.

However, the abnormality determination based on the purification rate cannot distinguish the abnormality of the catalyst in the SCR device from the abnormality of the urea water spraying system. If the piping is clogged due to the deep freezing of the urea water, this clogging should not be determined to be an abnormal situation immediately; rather, thawing is awaited, and then dosing is carried out. To date, however, there is a problem, i.e., it is not possible to determine whether the clogging is caused by a foreign matter or by the freezing.

SUMMARY OF THE INVENTION

An object of the present invention is to overcome the above-described problems, and to provide a urea water pipe clogging detection device for urea SCR, that can accurately detect whether the urea water pipe extending to the dosing valve adapted to spray urea water is clogged or not In order to achieve the above-mentioned object, the present invention provides a urea water pipe clogging detection device for urea SCR configured to suck urea water from a urea water tank with a supply pump, spray the urea water from a dosing valve disposed upstream of an SCR device via a pressurized urea water feed line, and detect clogging of a pipe segment that extends to the dosing valve from the supply pump, including: a urea water sensor configured to detect urea water temperature in the urea water tank; a pressure sensor configured to detect pressure of the pressurized urea water feed line; an exhaust gas temperature sensor disposed on an exhaust pipe upstream of the SCR device; and a clogging determination unit configured to perform startup control for driving the supply pump and increasing the pressure in the pipe segment upon turning on of a key switch, and then perform emptying control for returning the urea water from the pipe segment to the urea water tank if a detection value of the exhaust gas temperature sensor is less than or equal to a predetermined temperature and a detection value of the urea water sensor is greater than or equal to a freezing temperature. The clogging determination unit detects the clogging of the pipe segment from the detection value of the pressure sensor during the emptying control.

Preferably, the clogging determination unit is configured to drive a thawing unit for causing an engine cooling water to flow into the urea water tank and the dosing valve so as to thaw frozen urea when the urea water temperature detected by the urea water sensor is equal to or lower than the freezing temperature.

Preferably, the clogging determination unit performs the emptying control when it is determined from the detection value of the pressure sensor that the startup control is performed in a stable manner and the clogging determination on the pipe segment is not carried out.

Preferably, the clogging determination unit determines that there is no clogging if the pressure detected by the pressure sensor during the emptying control falls in a normal range, and then finishes the clogging determination on the pipe segment.

Preferably, the clogging determination unit makes a count-up to a count of clogging determination if the pressure detected by the pressure sensor during the emptying control is negative pressure and does not fall in the normal range, and the negative pressure continues over a predetermined time. Preferably, the clogging determination unit repeats the startup control and the emptying control when a predetermined period elapses subsequent to the count-up. Preferably, the clogging determination unit determines that the clogging has occurred with a foreign matter when the count of the clogging determination reaches a prescribed number.

The present invention forcibly carries out the emptying control, which is generally carried out while the vehicle is halting, upon turning on of the key switch under a prescribed condition for permission. During the emptying control, the present invention detects the clogging of the pipe segment based on the suction pressure of the supply pump. Thus, the present invention demonstrates an excellent advantage that the clogging due to a foreign matter, excluding the clogging due to the freezing, is accurately detected.

DETAILED DESCRIPTION

Preferred embodiments of the present invention will be described in detail with reference to the accompanying drawings.

Figure 1:
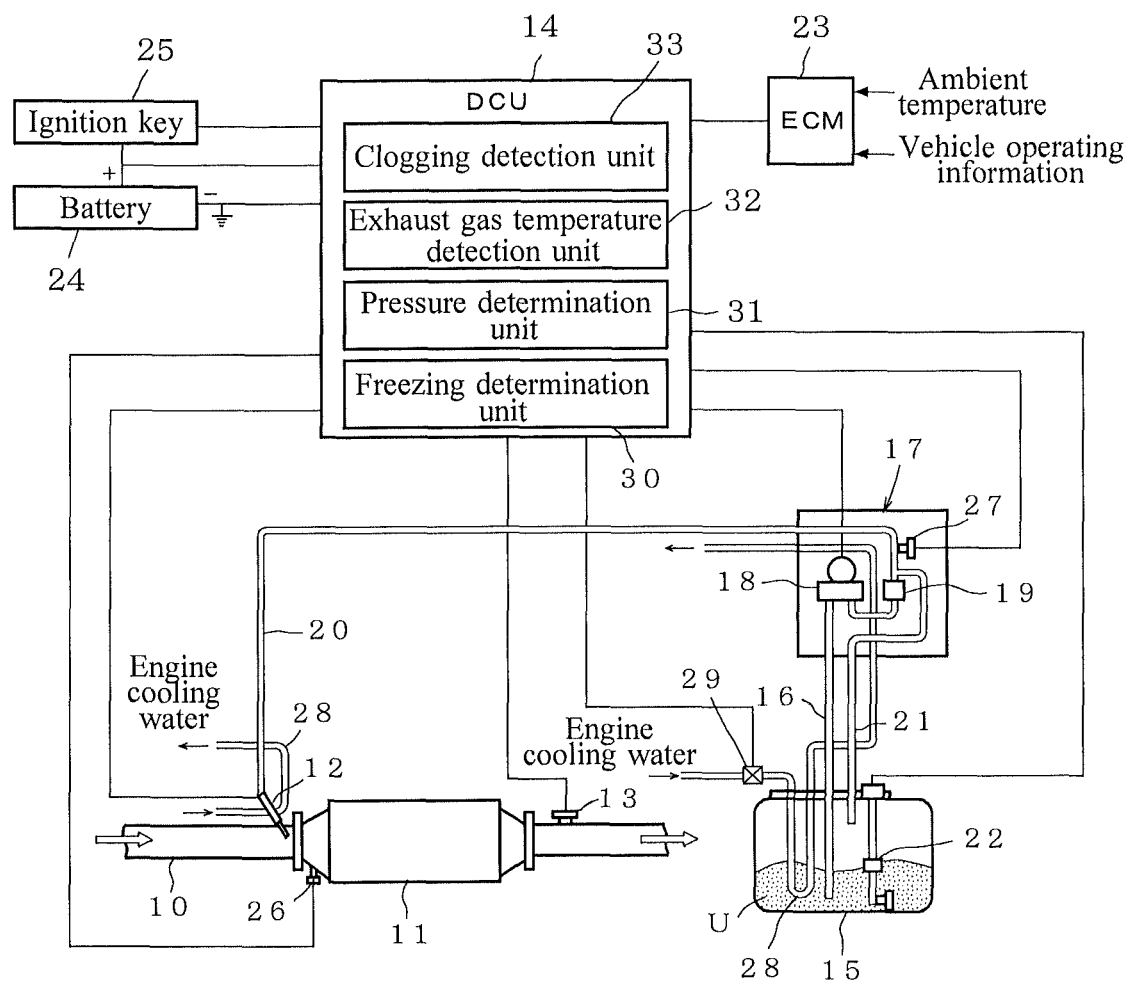
FIG. 1 is a schematic view of an SCR system according to one embodiment of the present invention.

FIG. 1 illustrates a schematic configuration of an SCR system. An SCR device 11 is connected to an exhaust pipe 10 of a diesel engine (not shown), a dosing valve 12 is disposed upstream of the SCR device 11 for spraying (injecting) urea water, and a NOx sensor 13 is disposed downstream of the SCR device 11.

A detection value of the NOx sensor 13 is entered to a DCU (dosing control unit) 14, and closing and opening of the dosing valve 12 is controlled by the DCU 14.

Urea water U to be sprayed from the dosing valve 12 is retained (pooled) in a urea water tank 15. The urea water U is sucked in by a supply pump 18 of a supply module 17 via a suction line 16. Foreign matters are removed from the urea water by a filter 19, and the pressurized urea water U is sent to the dosing valve 12 from the supply pump 18 via a pressurized urea water feed line 20. Excessive urea water U is returned to the urea water tank 15 from the pressurized urea water feed line 20 via a return line 21 on the exit side of the filter 19.

Although not shown, a four-way valve is connected to the supply pump 18 for switching between the suction side and the discharge side. A pressure sensor 27 is disposed on the pressurized urea water feed line 20 for detecting the pressure of the urea water. The detection value of the pressure sensor is introduced to the DCU 14.

A urea water sensor 22 is provided in the urea water tank 15 for detecting the urea water surface, the urea water temperature, the quality based on the concentration of the urea water, and the like. The urea water sensor 22 measures the urea water temperature and the like in the urea water tank 15, and sends the measurement results to the DCU 14.

The DCU 14 calculates a volume (amount) of urea water to be sprayed to the SCR device 11 and timing of spraying the urea water. The DCU 14 drives the supply pump 18 to increase the pressure of the urea water to prescribed pressure, and controls the opening and closing of the dosing valve 12 to spray an appropriate volume of urea water at appropriate timing.

In order to monitor that the urea water is appropriately sprayed from the dosing valve 12 and therefore the NOx value in the exhaust gas downstream of the SCR device 11 has a stable value, the NOx sensor 13 sends a measurement value to the DCU 14.

The DCU 14 is connected to an ECM (engine control module) 23, which is primarily provided for fuel injection control, and vehicle operating information such as a vehicle speed signal and ambient temperature is sent to the DCU 14 from the ECM 23.

The DCU 14 is also connected to a battery 24, and an ON signal and an OFF signal of a key switch of an ignition key 25 are entered to the DCU 14.

An exhaust gas temperature sensor 26 is disposed on the exhaust pipe 10 upstream of the SCR device 11 for detecting the temperature of the exhaust gas flowing into the SCR device 11. The detection value of the exhaust gas temperature sensor is introduced to the DCU 14.

A thawing pipe (defrosting pipe) 28 is disposed in the urea water tank 15 for causing the engine cooling water to flow for thawing when the urea water freezes, for example, in winter. Also, another thawing pipe 28 is provided on the dosing valve 12. The thawing pipe 28 has a thawing valve 29, which is thawing means. The thawing valve 29 is controlled by the DCU 14.

In this SCR system, the DCU 14 decides an instruction for a volume of urea water to be sprayed (instructed spray volume) from the dosing valve 12 on the basis of the information of the ECM 23 such that a detection value of the NOx sensor 13 becomes stable (becomes a desired value). The DCU 14 controls the opening and closing of the dosing valve 12 on the basis of the decided volume such that the urea water is sprayed in accordance with NOx contained in the exhaust gas. As the urea water is sprayed, the urea water is hydrolyzed in the SCR device 11, and becomes ammonia. The ammonia denitrifies NOx in the presence of the catalyst in the SCR device 11.

In an ordinary SCR system, the startup control of the supply pump 18 is executed after the key switch is turned on by the ignition key 25. The startup control causes the urea water to flow in the pressurized urea water feed line 20, and fills the pipe segment with the urea water thereby increasing the urea water pressure to the startup pressure.

After the startup control, a buildup control is performed for raising the urea water pressure to the buildup pressure. The buildup pressure is pressure ready for spraying. After the buildup control, the urea water is sprayed from the dosing valve 12 to remove NOx while the vehicle is traveling.

Subsequently, the ignition key 25 is turned off to stop the vehicle. Then, the dosing valve 12 is opened, and the four-way valve of the supply pump 18 is switched to perform emptying (empting) control for recovering the urea water, which remains in the pressurized urea water feed line 20, to the urea water tank 15 for a predetermined period. After that, the supply pump 18 is deactivated.

It should be remembered that if the piping from the supply pump 18 to the dosing valve 12 via the pressurized urea water feed line 20 is clogged with the freezing, a foreign matter or the like, the detection value of the NOx sensor 13 alone cannot determine whether or not the urea water is sprayed appropriately from the dosing valve 12.

With regard to the freezing of the urea water, the DCPU 14 carries out the following control. When the DCU 14 determines from the ambient temperature information from the ECM 23 and the urea water temperature of the urea water sensor 22 that the urea water temperature drops to a value close to the freezing temperature of the urea water (the freezing temperature depends on the urea water concentration, and it is −11 degrees C. in case of the normal concentration of 32.5%), the DCU 14 performs the thawing control, i.e., the thawing valve 29 or the thawing unit is opened to cause the engine cooling water to flow in the thawing pipes 28 thereby heating the dosing valve 12 and the urea water tank 15. If part of the frozen urea water remains in the pressurized urea water feed line 20 or the like, it may behave like a foreign matter to cause the clogging.

In order to deal with this, the DCU 14 in the embodiment of the present invention includes a freezing detection unit 30 for detecting presence and absence of the freezing of the urea water based on the ambient temperature from the ECM 23 and the detection value from the urea water sensor 22, a pressure determination unit 31 for receiving the detection value from the pressure sensor 27 and detect from the pressure (discharge pressure) during the startup control whether the startup control is stably carried out or whether the pressure (suction pressure) during the emptying control falls in a normal range, an exhaust gas temperature detection unit 32 for receiving the detection value from the exhaust gas temperature sensor 26, and a clogging determination unit 33 for carrying out the startup control to drive the supply pump 18 and raise the fluid pressure in the piping such as the pressurized urea water feed line 20 upon turning on of the key switch of the ignition key 25, then for carrying out the emptying control to cause the urea water to return to the urea water tank from the piping if the detection value of the exhaust gas temperature sensor 26 is equal to or lower than a prescribed temperature and the detection value of the urea water sensor 22 is equal to or higher than the freezing temperature, and for detecting the clogging of the piping from the detection value of the pressure sensor 27 during the emptying control.

The clogging determination unit 33 will further be described. The clogging determination is made immediately after the urea water pressure reaches the target pressure (startup pressure) in the startup control. At this point in time, it should be confirmed that the exhaust gas temperature is no higher than the predetermined value (temperature C of the DPF (diesel particulate filter)) and the prescribed condition for permission is not met.

When the prescribed condition for permission is met, the clogging determination unit 33 performs the emptying control. If the pressure during the emptying control, which is monitored by the pressure determination unit 31, falls in the normal range, the clogging determination unit determines that there is no clogging. If the pressure during the emptying control does not fall in the normal range and the pressure (negative pressure) continues to be below a threshold over a predetermined period, then the clogging determination unit determines that there is clogging. In case of no clogging, the dosing valve 12 is not closed, and the pressure becomes negative pressure, which is smaller than pressure in case of clogging. In case of clogging, the pressure becomes close to vacuum pressure, and therefore it is easy to determine whether the clogging has occurred or not.

When the clogging determination unit 33 determines that there is no clogging, the normal control is performed. The startup control is performed, and the metering control (the pressure of the urea water in the pressurized urea water feed line 20 is raised to a predetermined pressure, i.e., buildup pressure, from the startup control pressure to establish the ready-to-spray condition) is performed.

When the clogging determination unit 33 determines that there is clogging, the startup control is performed upon elapse of a predetermined period. When the urea water pressure reaches the target pressure, then the clogging determination is made again. The clogging determination for detecting presence and absence of the clogging is continuously performed a predetermined number of times (N times). If the clogging determination unit determines that there is no clogging during the N times of determination, it determines that the urea water, which is partially frozen, is thawed and the urea water has returned to a normal condition. If the clogging determination unit determines that the clogging continues over the N times of determination, it determines that the clogging is not caused by the freezing, but caused by a foreign matter. Thus, it is possible to distinguish the clogging caused by the foreign matter from the clogging caused by the freezing.

Figure 2A:
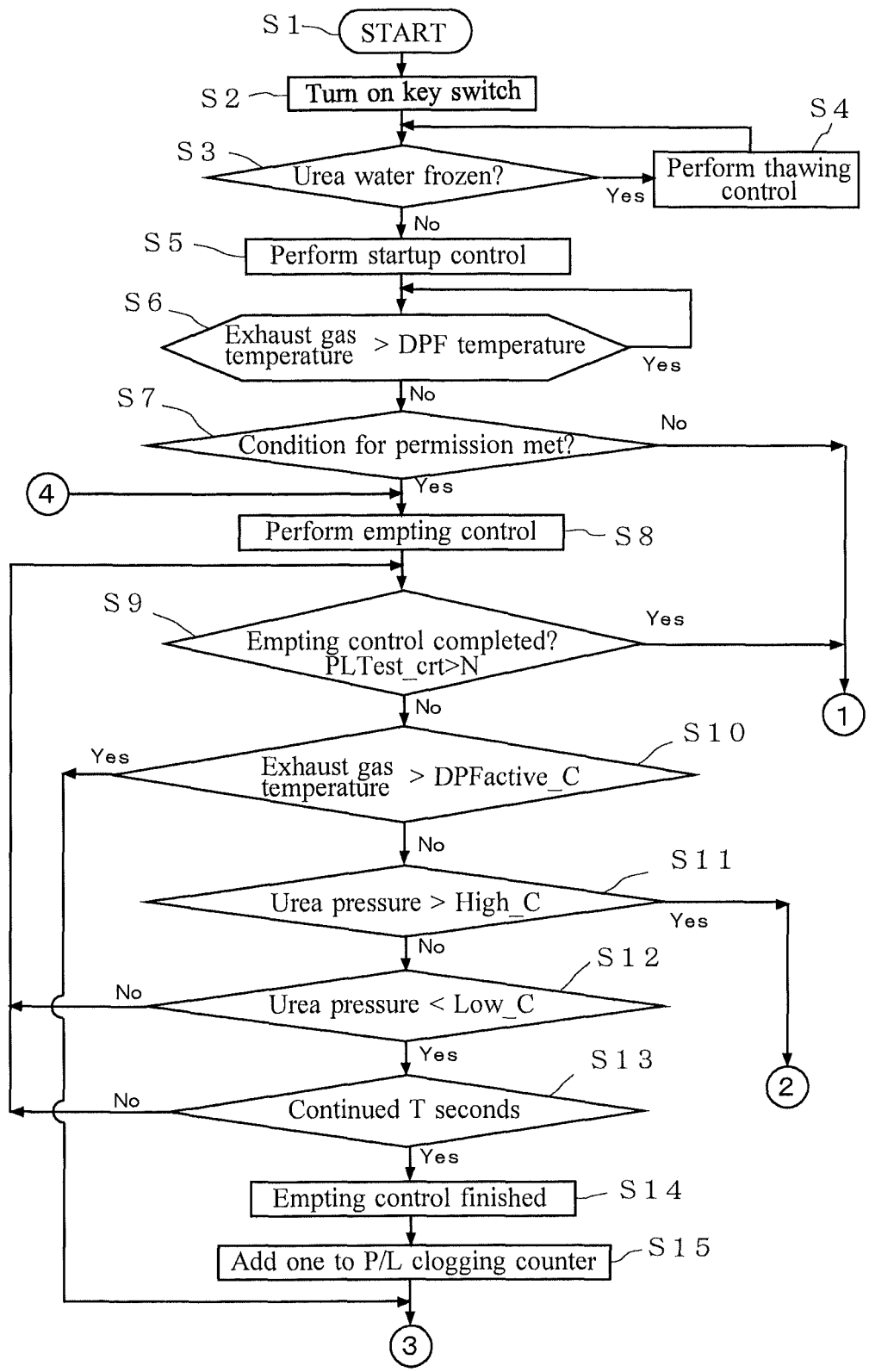
FIG. 2a, FIG. 2b and FIG. 2c represent a continuous flowchart illustrating a urea water pipe clogging detection device for urea SRC according to the embodiment of the present invention.
Figure 2B:
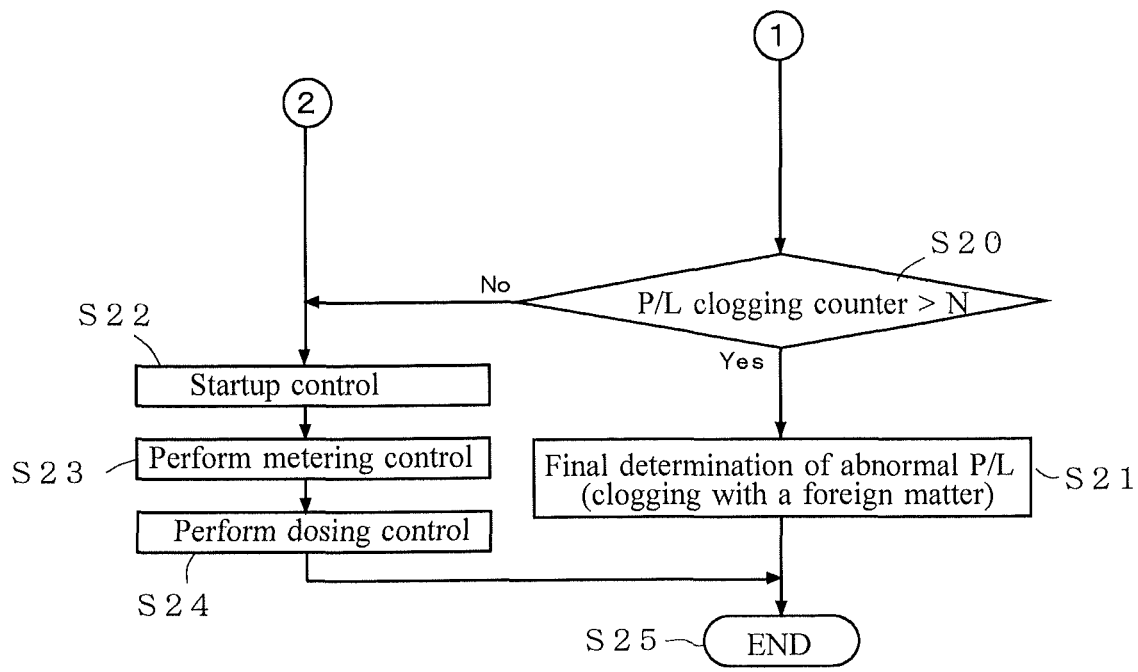
Figure 2C:
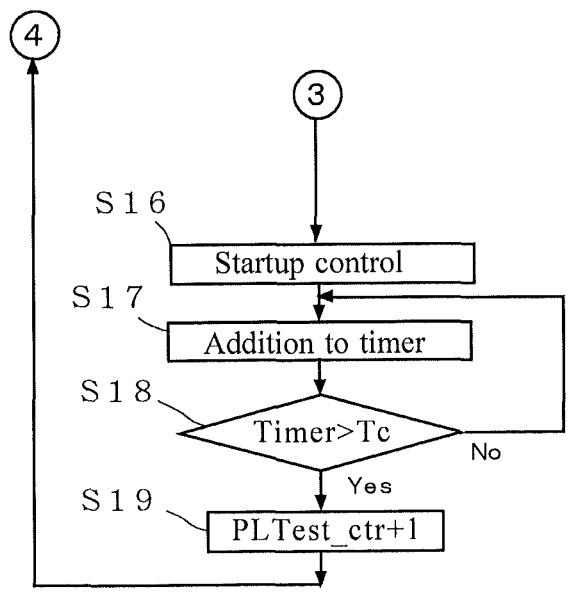

Now, the embodiment of the present invention will be described with reference to the flowchart of FIG. 2a, FIG. 2b and FIG. 2c.

At Step S1, the control starts. As the key switch is turned on at Step S2, it is determined at Step S3 whether freezing of the urea water has occurred or not. If the freezing has occurred (Yes), thawing (defrosting) control is performed at Step S4. If there is no freezing (No), the startup control is performed at Step S5, and it is determined at Step S6 whether the exhaust gas temperature is higher than the predetermined DPF temperature.

The determination of Step S6 is made to delay the clogging detection until the exhaust gas temperature drops from a high temperature. This is because if the exhaust gas temperature is high, and the emptying control is performed by opening the dosing valve immediately after the startup control, which feeds the urea water to the pressurized urea water feed line, then the urea water in the dosing valve becomes cyanuric acid and is crystalized due to the heat of the exhaust gas temperature. This would become a cause of clogging. To avoid it, the clogging detection is delayed until the exhaust gas temperature drops.

Subsequently, when the exhaust gas temperature drops at Step S6 (No), then it is determined at Step S7 whether the condition for permitting the emptying control is met or not.

Examples of the condition for permission include the following:

Failures that would halt the dosing have not occurred.
The startup control is performed stably.
Determination of pipe (PL) being clogged has not been made yet (count of the P/L clogging determination finishing counter is zero).
The freezing determination time at Step S3 is long or the SCR system is restarted upon thawing failure (possibly the freezing is incomplete).
The ambient temperature is equal to or below a predetermined value. The urea water temperature is equal to or below a predetermined value.
When the NOx purification rate drops (appropriate spraying of urea is not performed due to a foreign matter).

When one of these conditions is met (Yes), the emptying control is performed at Step S8. If none of the conditions is met (No), the control proceeds to Step S20.

After the emptying control is performed at Step S8, it is determined at Step S9 whether the emptying control is completed or not. It is determined again at Step S10 whether or not the exhaust gas temperature is higher than the temperature DPFactive_C. If the exhaust gas temperature is higher than the temperature DPFactive_C (Yes), the control proceeds to Step S16 to perform the startup control.

When the exhaust gas temperature is not high at Step S10 (No), then it is determined whether the urea pressure is higher than an upper limit (High_C) of the normal range. If the urea pressure is higher than the upper limit of the normal range (Yes), the startup control is executed at Step S22.

If it is determined at Step S11 that the urea pressure of the urea water is equal to or smaller than the upper limit (No), then it is determined at Step S12 whether the urea pressure is equal to the lower limit (Low_C) of the normal range. If the urea pressure is greater than the lower limit (No), the control returns to the determination of Step S9. If the urea pressure is smaller than the lower limit (Yes), it is then determined at Step S13 whether this situation continues for T seconds. If this situation does not continue for T seconds (No), the control returns to the determination of Step S9. If this situation continues for T seconds (Yes), the emptying control is performed at Step S14, and then the count of the P/L clogging counter is incremented +1 at Step S15. Subsequently, the startup control is resumed at Step S16. The timer addition is made at Step S17 and the timer count up is made at Step S18. When the time exceeds Tc (Yes), one is added to the count of the PL test counter (PLtest_ctr) at Step S19. After that, the emptying control is executed again at Step S8.

Thus, when the piping such as the pressurized urea water feed line is clogged with a foreign matter or the like, Steps S9 to S19 are repeated. When this repeating exceeds the prescribed number N, then it is determined at Step S9 that the emptying control is completed. The control then proceeds to Step S20.

It is determined at Step S20 whether the count of the P/L clogging counter is equal to or greater than N. If the count is greater than N (Yes), a final determination is made at Step S21 that determines the P/L being abnormal (clogging with a foreign matter). Then, the control is finished (Step S25).

If it is determined at Step S20 that the count of the P/L clogging counter is no greater than N, then the startup control is performed at Step S22, the metering control is performed at Step S23, and the dosing control is performed at Step S24. Thus, the control is finished as the normal control (Step S25). In this case, the clogging determination unit 33 can also determine from the count of the P/L clogging counter that the clogging is caused by partial freezing and subsequently the thawing is completed.

What is claimed is:

1. A urea water pipe clogging detection device for urea selective catalytic reduction configured to suck urea water from a urea water tank with a supply pump and spray the urea water from a dosing valve disposed upstream of an selective catalytic reduction device via a pressurized urea water feed line, and detect clogging of a pipe segment that extends to the dosing valve from the supply pump, said urea water pipe clogging detection device comprising:
a urea water sensor configured to detect urea water temperature in the urea water tank;
a pressure sensor configured to detect pressure of the pressurized urea water feed line;
an exhaust gas temperature sensor disposed on an exhaust pipe upstream of the selective catalytic reduction device; and
a clogging determination unit configured to perform startup control for driving the supply pump and increasing pressure in the pipe segment upon turning on of a key switch, and then perform emptying control for returning the urea water from the pipe segment to the urea water tank if a detection value of the exhaust gas temperature sensor is less than or equal to a predetermined temperature and a detection value of the urea water sensor is greater than or equal to a freezing temperature, the clogging determination unit being configured to detect the clogging of the pipe segment from the detection value of the pressure sensor during the emptying control.

2. The urea water pipe clogging detection device for urea selective catalytic reduction according to claim 1, wherein the clogging determination unit is configured to drive a thawing unit for causing an engine cooling water to flow into the urea water tank and the dosing valve so as to thaw frozen urea when the urea water temperature detected by the urea water sensor is equal to or lower than the freezing temperature.

3. The urea water pipe clogging detection device for urea selective catalytic reduction according to claim 2, wherein the clogging determination unit performs the emptying control when it is determined from a detection value of the pressure sensor that the startup control is performed in a stable manner and clogging determination on the pipe segment is not carried out.

4. The urea water pipe clogging detection device for urea selective catalytic reduction according to claim 2, wherein the clogging determination unit determines that there is no clogging if the pressure detected by the pressure sensor during the emptying control falls in a normal range, and then finishes the clogging determination on the pipe segment.

5. The urea water pipe clogging detection device for urea selective catalytic reduction according to claim 2, wherein the clogging determination unit makes a count-up to a count of clogging determination if the pressure detected by the pressure sensor during the emptying control is negative pressure and does not fall in a normal range, and the negative pressure continues over a predetermined time, the clogging determination unit repeats the startup control and the emptying control when a predetermined period elapses subsequent to the count-up, and the clogging determination unit determines that the clogging has occurred with a foreign matter when the count of the clogging determination reaches a prescribed number.

6. The urea water pipe clogging detection device for urea selective catalytic reduction according to claim 1, wherein the clogging determination unit performs the emptying control when it is determined from a detection value of the pressure sensor that the startup control is performed in a stable manner and clogging determination on the pipe segment is not carried out.

7. The urea water pipe clogging detection device for urea selective catalytic reduction according to claim 6, wherein the clogging determination unit determines that there is no clogging if the pressure detected by the pressure sensor during the emptying control falls in a normal range, and then finishes the clogging determination on the pipe segment.

8. The urea water pipe clogging detection device for urea selective catalytic reduction according to claim 6, wherein the clogging determination unit makes a count-up to a count of clogging determination if the pressure detected by the pressure sensor during the emptying control is negative pressure and does not fall in a normal range, and the negative pressure continues over a predetermined time, the clogging determination unit repeats the startup control and the emptying control when a predetermined period elapses subsequent to the count-up, and the clogging determination unit determines that the clogging has occurred with a foreign matter when the count of the clogging determination reaches a prescribed number.

9. The urea water pipe clogging detection device for urea selective catalytic reduction according to claim 1, wherein the clogging determination unit determines that there is no clogging if the pressure detected by the pressure sensor during the emptying control falls in a normal range, and then finishes the clogging determination on the pipe segment.

10. The urea water pipe clogging detection device for urea selective catalytic reduction according to claim 9, wherein the clogging determination unit makes a count-up to a count of clogging determination if the pressure detected by the pressure sensor during the emptying control is negative pressure and does not fall in the normal range, and the negative pressure continues over a predetermined time, the clogging determination unit repeats the startup control and the emptying control when a predetermined period elapses subsequent to the count-up, and the clogging determination unit determines that the clogging has occurred with a foreign matter when the count of the clogging determination reaches a prescribed number.

11. The urea water pipe clogging detection device for urea selective catalytic reduction according to claim 1 further including a freezing detection unit configured to detect whether the urea water is frozen in the pipe segment.

12. The urea water pipe clogging detection device for urea selective catalytic reduction according to claim 1 further including an ambient air temperature sensor for detecting temperature of ambient air.

13. The urea water pipe clogging detection device for urea selective catalytic reduction according to claim 1, wherein the clogging determination unit makes a count-up to a count of clogging determination if the pressure detected by the pressure sensor during the emptying control is negative pressure and does not fall in a normal range, and the negative pressure continues over a predetermined time, the clogging determination unit repeats the startup control and the emptying control when a predetermined period elapses subsequent to the count-up, and the clogging determination unit determines that the clogging has occurred with a foreign matter when the count of the clogging determination reaches a prescribed number.

* * * * *